United States Patent
Yamazaki

(10) Patent No.: US 10,514,364 B2
(45) Date of Patent: Dec. 24, 2019

(54) PREPARATIVE SEPARATION-PURIFICATION METHOD AND SYSTEM

(71) Applicant: SHIMADZU CORPORATION, Kyoto-shi, Kyoto (JP)

(72) Inventor: Tomoyuki Yamazaki, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 406 days.

(21) Appl. No.: 15/287,878

(22) Filed: Oct. 7, 2016

(65) Prior Publication Data

US 2018/0100834 A1 Apr. 12, 2018

(51) Int. Cl.

| | | |
|---|---|---|
| G01N 30/14 | (2006.01) | |
| B01D 15/42 | (2006.01) | |
| G01N 30/06 | (2006.01) | |
| B01D 15/10 | (2006.01) | |
| B01D 15/12 | (2006.01) | |

(52) U.S. Cl.
CPC ............ G01N 30/14 (2013.01); B01D 15/10 (2013.01); B01D 15/12 (2013.01); B01D 15/424 (2013.01); G01N 30/06 (2013.01); *G01N 2030/143* (2013.01)

(58) Field of Classification Search
CPC .. G01N 30/14; G01N 2030/143; G01N 30/06; B01D 15/10; B01D 15/424; B01D 15/245; B01D 15/12
See application file for complete search history.

(56) References Cited

U.S. PATENT DOCUMENTS 3,859,209 A * 1/1975 Jahnsen ................ G01N 30/12
                                                      210/180
2013/0273586 A1* 10/2013 Turino ............... G01N 30/7233
                                                       435/23

(Continued)

FOREIGN PATENT DOCUMENTS

JP     1-142463 A   6/1989
JP     02-122260 A  5/1990

(Continued)

OTHER PUBLICATIONS

Communication dated May 30, 2017 from the Japanese Patent Office in counterpart Application No. 2014-055587.

*Primary Examiner* — Benjamin L Lebron
(74) *Attorney, Agent, or Firm* — Sughrue Mion, PLLC

(57) ABSTRACT

Provided is a preparative separation-purification method in which an eluting solvent is passed through a trap column 20 to elute a target component captured in the trap column and collect the target component through a collection passage 34 into a collection container 21, the method including: a process of transferring the eluting solvent containing the eluted target component from the trap column to the collection container through the collection passage; a process of suctioning the eluting solvent remaining in the collection passage through a suction passage 6 connected to the collection passage; and a process of removing the collection passage from the trap column and the collection container. By this method, the eluate or eluting solvent remaining in the collection passage is prevented from being dropped into the collection container. A backflow of the eluate into the trap column is also prevented.

6 Claims, 3 Drawing Sheets

(56) References Cited

U.S. PATENT DOCUMENTS

2013/0295597 A1* 11/2013 DeWitte ................ G01N 30/06
                        435/23
2013/0306536 A1* 11/2013 Yamazaki ............ B01D 15/245
                        210/198.2

FOREIGN PATENT DOCUMENTS

| JP | 2003-149217 A | 5/2003 |
| JP | 2013-238471 A | 11/2013 |

* cited by examiner

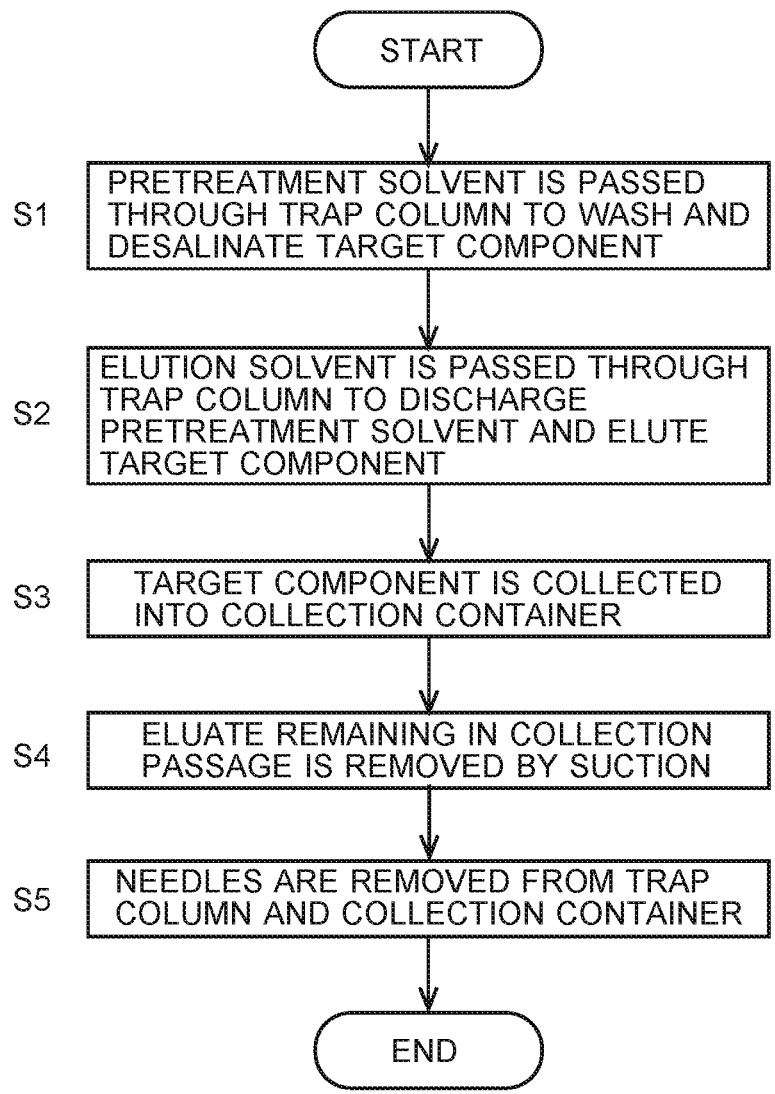

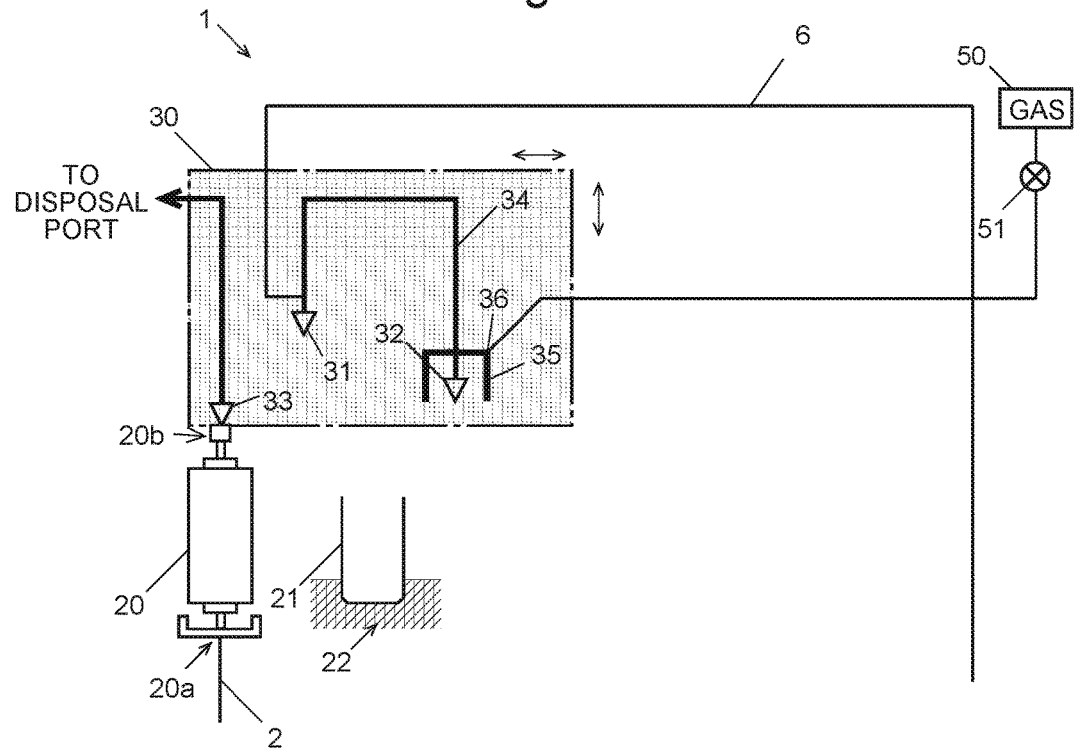
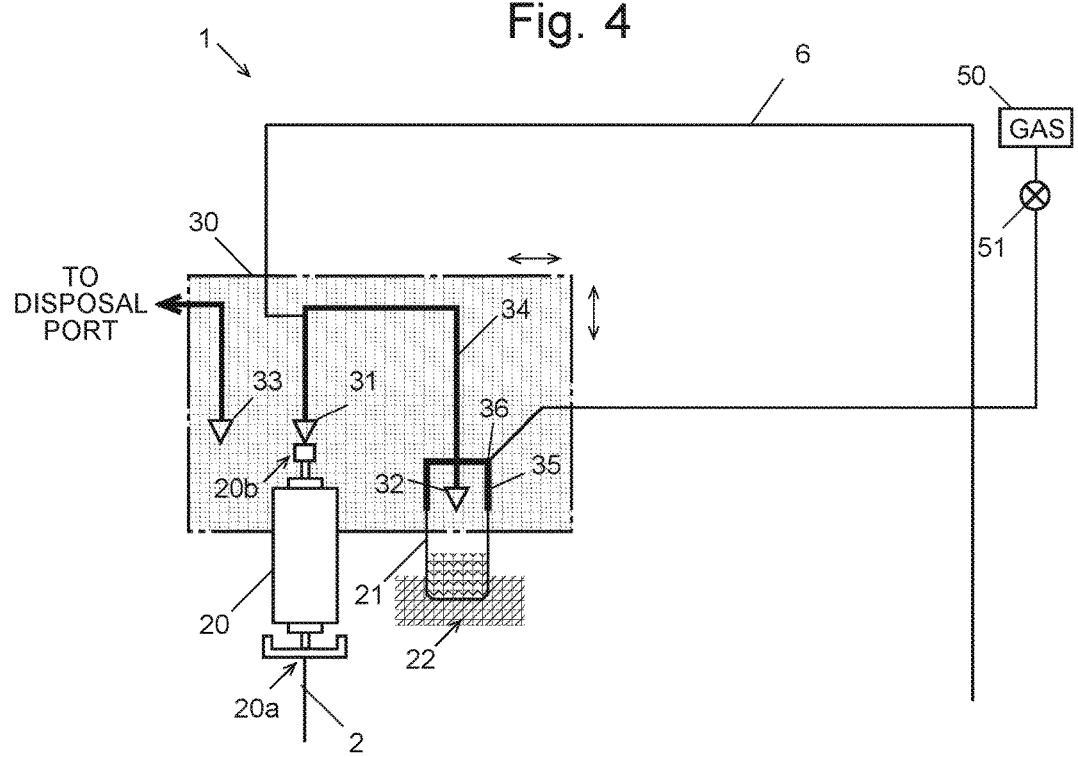

PREPARATIVE SEPARATION-PURIFICATION METHOD AND SYSTEM

TECHNICAL FIELD

The present invention relates to a preparative separation-purification method and system for purifying and collecting each component in a sample separated by a preparative separation liquid chromatograph or similar device.

BACKGROUND ART

As one method for purifying and collecting a desired component contained in a sample, a technique which uses a preparative separation liquid chromatograph is known (for example, see Patent Literatures 1 and 2). According to this method, each of the components that need to be purified and collected ("target components") among the components in a sample separated by a separation column is initially captured in a separate trap column.

Subsequently, an eluting solvent is poured into the trap column from its inlet end to elute the target component into the eluting solvent. The eluting solvent containing the eluted target component (this solvent is hereinafter called the "eluate") is extracted from the outlet end of the trap column and transferred to a collection container. Ultimately, the solvent in the eluate is vaporized in the collection container to obtain the target component in the form of dry powder (solid).

For the transfer of the eluate from the trap column to the collection container, a tube having two needles connected to both ends is normally used, with the tip of one needle inserted into the outlet end of the trap column and that of the other needle inserted into the inlet end of the collection container. In this state, the eluting solvent is additionally introduced from the inlet end of the trap column to extrude the eluate (i.e. the eluting solvent containing the target component) from the outlet end of the trap column. The extruded eluate enters the needle inserted into the outlet end of the trap column and passes through the aforementioned tube, to be dropped into the collection container from the tip of the needle inserted into the inlet end of the collection container. The collected eluate is dried to obtain the target component in the form of powder.

CITATION LIST

Patent Literature

Patent Literature 1: JP 2-122260 A
Patent Literature 2: JP 2003-149217 A

SUMMARY OF INVENTION

Technical Problem

In the previously described technique, after the target component is processed into a powdery form, when the two needles are removed from the trap column and the collection container, the eluate or eluting solvent remaining in the tube is dropped from the tip of the needle into the collection container and damages the dried state of the target component. The eluate may also be dropped into the trap column and cause the problem of contamination in the subsequent preparative separation process.

The present invention has been developed in view of the previously described point. Its objective is to provide a preparative separation-purification method and system in which the eluate or eluting solvent remaining in the tube is prevented from being dropped into the collection container, and a backflow of the eluate into the trap column is also prevented, in the process of collecting a target component captured in a trap column into a collection container.

Solution to Problem

The preparative separation-purification method according to the present invention developed for solving the previously described problem is a preparative separation-purification method in which an eluting solvent is passed through a trap column to elute a target component captured in the trap column and collect the target component through a collection passage into a collection container, the method including:

a) a collection process in which the eluting solvent containing the eluted target component is transferred from the trap column to the collection container through the collection passage;

b) a suction process in which the eluting solvent remaining in the collection passage after the collection process is suctioned through a suction passage connected to the collection passage; and c) a removal process in which the collection passage is removed from the trap column and the collection container after the suction process.

In the previously described preparative separation-purification method, after the collection process has been completed, the eluting solvent remaining in the collection passage is suctioned through the suction passage before the collection passage is removed from the trap column and the collection container. Normally, the end of the collection passage inserted into the collection container is open to the ambient air. Accordingly, when the eluting solvent in the collection passage is suctioned through the suction passage, the air in the collection container flows into the collection passage, and the eluting solvent remaining in the collection passage between the suction point and the collection container can be easily removed. Therefore, no dropping of the eluting solvent into the collection container occurs in the subsequent process of removing the collection passage from the collection container. For such a mechanism to work, the eluting solvent remaining in the collection passage does not always need to be completely removed in the suction process; the minimal requirement is to prevent the eluting solvent from remaining in the tip portion inserted into the collection container.

In the suction process, the suction passage may preferably be connected to the collection passage at a position close to the needle inserted into the outlet end of the trap column. By this configuration, the eluting solvent remaining in the tip portion of the collection passage inserted in the trap column can also be removed in a greater quantity in the suction process. Therefore, no solvent will be dropped into the trap column when the collection passage is removed from the collection container.

Furthermore, in the collection process, a diluting liquid may be supplied to the collection passage via the suction passage according to necessity. This operation prevents the deposition of the target component in the eluate within the collection passage, which can occur if the eluate contains a high concentration of the target component.

The preparative separation-purification system according to the present invention developed for solving the previously described problem is a preparative separation-purification system for passing an eluting solvent through a trap column to elute a target component captured in the trap column and collect the target component through a collection passage into a collection container, the system including:

a) an elution liquid supply passage to be connected to an inlet end of the trap column, for supplying the eluting solvent;

b) a collection passage for connecting an outlet end of the trap column and an inlet end of the collection container, and c) a suction passage having a first end connected to an intermediate portion of the collection passage and a second end configured to be connected with a suction pump.

Advantageous Effects of the Invention

As just described, with the preparative separation-purification method and system according to the present invention, the eluting solvent remaining in the collection passage (tube) is prevented from being dropped into the collection container, so that a target component in a satisfactorily dried state can be obtained. A backflow of the eluting solvent from the collection passage into the trap column can also be prevented.

BRIEF DESCRIPTION OF DRAWINGS

FIG. 2 is a flowchart of one embodiment of the preparative separation-purification method according the present invention.

FIG. 3 is a diagram showing the connection state of the passages in the process of collecting a target component and suctioning the liquid remaining in the collection passage.

FIG. 4 is a diagram showing the connection state of the passages in the process of pretreating and eluting a target component.

DESCRIPTION OF EMBODIMENTS

Figure 1:
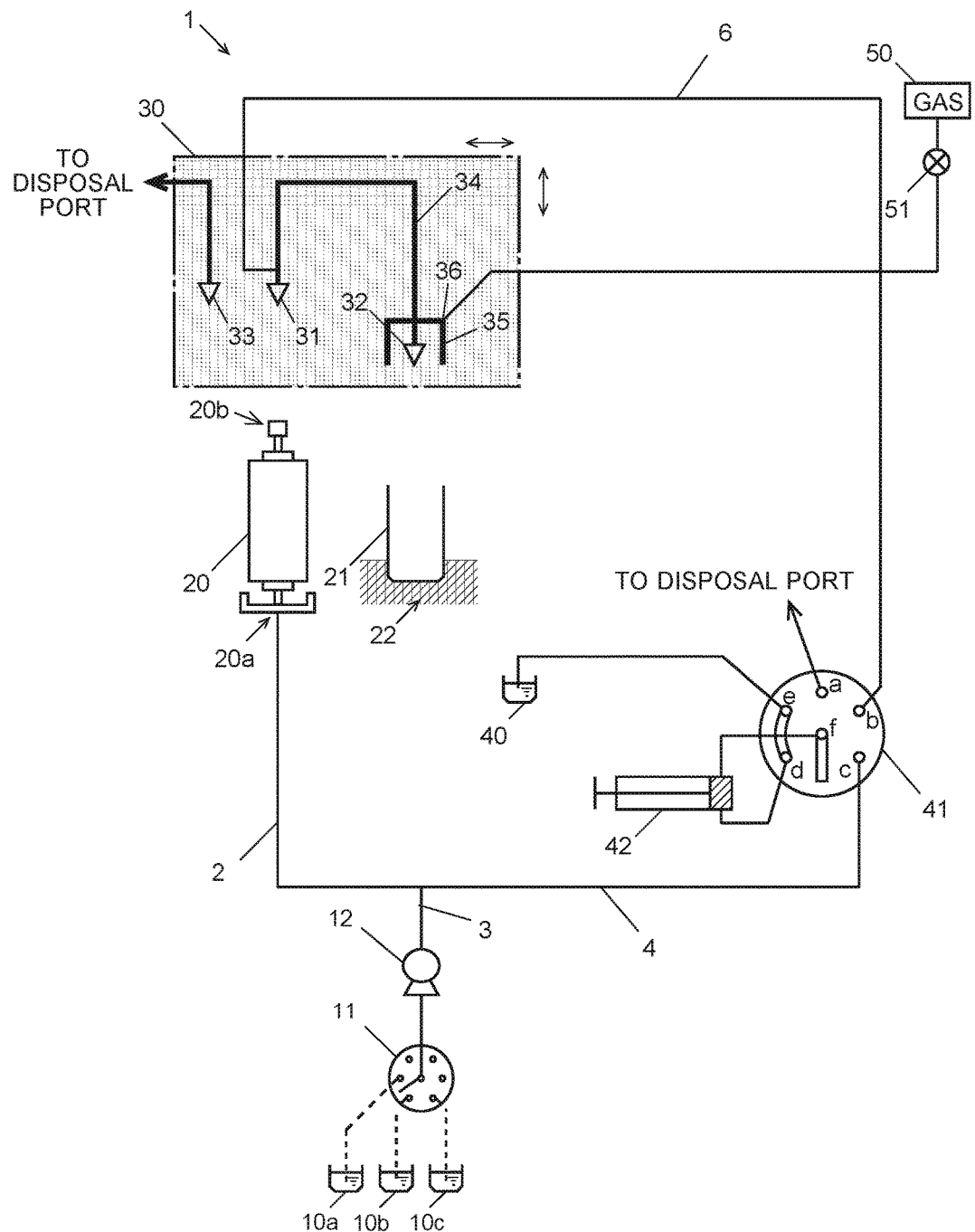
FIG. 1 is a schematic diagram showing one embodiment of the preparative separation-purification system according to the present invention.

One embodiment of the preparative separation-purification system and separation-purification method according to the present invention is hereinafter described with reference to the attached drawings. It should be noted that some components (pumps, passage-switching units, etc.) that are not characteristic components of the preparative separation-purification system according to the present invention are appropriately omitted from the drawings.

FIG. 1 is a schematic configuration diagram of one embodiment of the preparative separation-purification system according to the present invention. The preparative separation-purification system 1 in the present embodiment is a system for collecting, into a collection container 21, a sample component eluted from a trap column 20 which holds the target component separated from the other components of the sample by a liquid chromatograph system (not shown).

The trap column 20 contains a packing material on which the target component is captured. The collection container 21 is a container for receiving drops of an eluate from the trap column 20 and for drying the eluate to collect the target component. A heater 22 is provided to accelerate the drying process by heating the collection container 21.

A solvent supply passage 2 is connected to the inlet end 20a of the trap column 20 in which the target component is captured. The solvent supply passage 2 is branched into a pretreatment solvent supply passage 3 and an eluting solvent supply passage 4 at its upstream end.

Three containers 10a, 10b and 10c, which respectively hold three kinds of pretreatment solvents, are connected via a liquid-sending pump 12 and a first passage-switching unit 11 to the pretreatment solvent supply passage 3. In the present embodiment, acetonitrile, ammonia water and pure water are used as the pretreatment solvents.

The eluting solvent supply passage 4 is connected to port c of a second passage-switching unit 41. The second passage-switching unit 41 has five ports a through e and one common port f. The six ports a through f are respectively connected to a disposal port, suction passage 6, eluting solvent supply passage 4, measuring pump 42, eluting solvent container 40, and measuring pump 42. In the present embodiment, DCM (dichloromethane) is used as the eluting solvent. As will be explained later, the measuring pump 42 doubles as a suction pump.

The suction passage 6 extending from port b of the second passage-switching unit 41 is connected to a fraction collector head 30 which can be horizontally and vertically driven by a drive mechanism (not shown). The fraction collector head 30 includes a collection passage 34 with a first needle 31 and a second needle 32 provided at both ends as well as a disposal passage with a third needle 33 at its tip. The third needle 33 is connected with the disposal port. The aforementioned suction passage 6 is connected to the collection passage 34 at a position close to the first needle 31. As will be described later, the collection passage 34 is configured so that the tip of the second needle 32 is positioned at a lower level than the tip of the first needle 31 when the first and second needles 31 and 32 are respectively connected to the outlet end 20b of the trap column 20 and the inlet end 20a of the collection container 21. Additionally, an attachment part 35 to be put on the inlet end of the collection container 21 so as to cover the tip of the second needle 32 is provided at the end of the collection passage 34 at which the second needle 32 is connected. A gas ejection port 36 is formed in the attachment part 35. The gas ejection port 36 is connected with a gas supply unit 50 via a valve 51. From this gas ejection port 36, a stream of gas for drying the eluate extracted from the second needle 32 is spouted.

An operation of the preparative separation-purification system 1 according to the present embodiment is hereinafter described with reference to the flowchart shown in FIG. 2.

Initially, as shown in FIG. 3, the fraction collector head 30 is driven so as to connect the solvent supply passage 2 to the inlet end 20a of the trap column 20 in which the target component is captured, as well as to connect the third needle 33 to the outlet end 20b of the same column. In this state, the liquid-sending pump 12 is energized and the first passage-switching unit 11 is operated so as to sequentially supply the three aforementioned kinds of pretreatment solvents to the trap column 20 to perform the pretreatment (washing and desalination) of the target component (Step S1). After passing through the trap column 20, the pretreatment solvents are discharged through the third needle 33 to the disposal port. In the present embodiment, acetonitrile and ammonia water are initially passed to wash the target component. After that, pure water is passed to desalinate the target component.

Subsequently, the second passage-switching unit 41 is switched so as to connect the measuring pump 42 and the eluting solvent container 40 which holds dichloromethane (i.e. port e is connected to port f), and the measuring pump 42 is operated to suction a measured amount of dichloromethane from the eluting solvent container 40. After that, the second passage-switching unit 41 is once more switched (to connect port c to port f), and the measuring pump 42 is operated to force the suctioned dichloromethane into the trap column 20 through its inlet end 20a. By this operation, the water which remains in the trap column 20 after being introduced for the purpose of washing is forced to the disposal port. Simultaneously, the target component captured in the trap column 20 is eluted into the dichloromethane (Step S2).

After the water remaining in the trap column 20 is discharged and the target component is eluted into the dichloromethane, the liquid-sending pump 12 is de-energized and the fraction collector head 30 is driven so as to insert the first needle 31 into the outlet end 20b of the trap column 20 and the second needle 32 into the inlet end of the collection container 21, as shown in FIG. 4. In this state, the eluting solvent containing the target component, i.e. the eluate, is dropped from the second needle 32 into the collection container 21 to collect the target component (Step S3).

While the eluate is being dropped into the collection container 21 heated by the heater 22 on its bottom and side surfaces, a predetermined kind of gas is spouted from the gas ejection port 36 in the attachment part 35 onto the drops of the eluate to promote the drying of the eluate. The spouted gas breaks the eluate into fine droplets and makes them adhere to the inner surface of the collection container 21. Since the side and bottom surfaces of the collection container 21 are heated by the heater 22, the dichloromethane is quickly vaporized and a dry powder of the target component is collected in the collection container 21. The flow rate and pressure of the spouted gas are regulated with the gas supply unit 50 and the valve 51. After the process of collecting the target component in the collection container 21 has been completed, the valve 51 is closed to discontinue the gas supply. It should be noted that the upper portion of the attachment part 35 is configured to allow the passage of gas to the outside so that the gas spouted into the collection container 21 can be discharged.

In the conventional case, the task of collecting the target component is completed at this stage, and the fraction collector head 30 is driven to remove the first needle 31 from the outlet end 20b of the trap column 20 and the second needle 32 from the inlet end of the collection container 21. However, at this point in time, the eluate still remains in the collection passage 34. Therefore, when the needles are removed, this eluate drops into the collection container 21 and the trap column 20.

In the present embodiment, this situation is avoided as follows: Before the first and second needles 31 and 32 are removed, the connection of the second passage-switching unit 41 is changed so as to connect the suction passage 6 and the measuring pump 42 (i.e. to connect port b and port f). Subsequently, the measuring pump 42 is energized to suction and remove the eluate remaining in the collection passage 34 (Step S4). As noted earlier, the collection container 21 allows the passage of gas between the inside and outside of the same container, with the inside maintained at the atmospheric pressure. Accordingly, in the suctioning process, a stream of air enters the collection passage 34 from the second needle 32, whereby the eluate in the passage 34 is removed.

Since the suction passage 6 is connected at a position near the first needle 31, the eluate remaining in the end portion of the collection passage 34 close to the first needle 31 can also be suctioned.

After the suctioning process has been completed, the fraction collector head 30 is driven to remove the first and second needles 31 and 32 (Step S5). There is no dropping of the eluate into the collection container 21 or trap column 20, since the eluate which was remaining in the collection passage 34 has already been removed in Step S4. Accordingly, the target component collected in the collection container 21 is maintained in the dried state. The problem of the contamination in the trap column 20 will not also occur when the next component is collected.

In the preparative separation-purification method according to the present invention, the suction passage 6 can also be utilized as follows:

If the eluate transferred from the outlet end 20b of the trap column 20 to the collection passage 34 contains the target component in high concentration, the target component may be easily deposited in the collection passage 34 and cause the clogging of the passage or other problems.

Accordingly, the connection state of the second passage-switching unit 41 is changed (to connect port b to port f) to introduce dichloromethane (i.e. eluting solvent) into the suction passage 6 according to necessity. By this operation, the eluting solvent which has been introduced into the collection passage 34 with a high concentration of the target component can be diluted to prevent the deposition of the target component.

The previously described embodiment is a mere example and can be appropriately changed within the spirit of the present invention. The kinds of pretreatment solvents or eluting solvent mentioned in the embodiment are mere examples and can be appropriately changed according to the kind of target component. The passage configuration shown in FIG. 1 is also a mere example and can be appropriately changed within the spirit of the present invention.

REFERENCE SIGNS LIST

1 . . . Preparative Separation-Purification System
2 . . . Solvent Supply Passage
3 . . . Pretreatment Solvent Supply Passage
4 . . . Eluting Solvent Supply Passage
6 . . . Suction Passage
10a, 10b, 10c . . . Pretreatment Solvent Container
11 . . . First Passage-Switching Unit
12 . . . Liquid-Sending Pump
20 . . . Trap Column
  20a . . . Inlet End
  20b . . . Outlet End
21 . . . Collection Container
22 . . . Heater
30 . . . Fraction Collector Head
  31 . . . First Needle
  32 . . . Second Needle
  33 . . . Third Needle
  34 . . . Collection Passage
  35 . . . Attachment Part
  36 . . . Gas Ejection Port
40 . . . Eluting Solvent Container
41 . . . Second Passage-Switching Unit
42 . . . Measuring Pump
50 . . . Gas Supply Unit
51 . . . Valve

The invention claimed is:

1. A preparative separation-purification method in which an eluting solvent is passed through a trap column to elute a target component captured in the trap column and collect the target component through a collection passage into a collection container, the method comprising:
   a) a collection process in which the eluting solvent containing the eluted target component is transferred from the trap column to the collection container through the collection passage;
   b) a suction process in which the eluting solvent remaining in the collection passage after the collection process is suctioned through a suction passage connected to the collection passage and is discharged outside the collection passage; and
   c) a removal process in which the collection passage is removed from the trap column and the collection container after the suction process, wherein
   atmospheric pressure is maintained inside the collection container during the suction process.

2. The preparative separation-purification method according to claim 1, wherein the suction passage is connected to a position close to a needle inserted into an outlet end of the trap column.

3. The preparative separation-purification method according to claim 1, wherein a diluting liquid is supplied to the collection passage via the suction passage in the collection process.

4. The preparative separation-purification method according to claim 2, wherein a diluting liquid is supplied to the collection passage via the suction passage in the collection process.

5. A preparative separation-purification system for passing an eluting solvent through a trap column to elute a target component captured in the trap column and collect the target component through a collection passage into a collection container, the system comprising:
   a) an elution liquid supply passage to be connected to an inlet end of the trap column, for supplying the eluting solvent;
   b) a collection passage for connecting an outlet end of the trap column and an inlet end of the collection container;
   c) a suction passage having a first end connected to an intermediate portion of the collection passage and a second end;
   d) a suction pump connected to the second end of the suction passage, the suction pump configured to suction the eluting solvent remaining in the collection passage through the suction passage and discharge the suctioned eluting solvent outside the collection passage; and
   e) the collection container, wherein
   the collection container is configured to allow passage of gas between an inside and outside of the collection container when the collection passage is connected to the inlet end of the collection container, such that atmospheric pressure is maintained inside the collection container while the suction pump suctions the eluting solvent remaining in the collection passage.

6. The preparative separation-purification system according to claim 5, further comprising:
   f) a diluting liquid supplier connectable to the second end of the suction passage in place of the suction pump, for supplying a diluting liquid for lowering a concentration of the target component contained in the eluting solvent.

* * * * *